United States Patent [19]

Glover et al.

[11] Patent Number: 4,809,537

[45] Date of Patent: Mar. 7, 1989

[54] SYSTEM AND METHOD FOR MONITORING WET BULB TEMPERATURE IN A FLUE GAS STREAM

[75] Inventors: Robert L. Glover, Lockport, N.Y.; Verle V. Bland, Evergreen, Colo.

[73] Assignee: Electric Power Research Institute, Inc., Palo Alto, Calif.

[21] Appl. No.: 5,109

[22] Filed: Jan. 20, 1987

[51] Int. Cl.$^4$ .................................................. G01N 31/00
[52] U.S. Cl. .................................... 73/29; 73/338; 236/44 A; 137/253
[58] Field of Search ................... 236/94, 44 R, 44 A, 236/15 E; 431/13; 34/50; 73/338, 29, 336, 5; 137/386, 253

[56] References Cited

U.S. PATENT DOCUMENTS

| | | | |
|---|---|---|---|
| 2,721,065 | 10/1955 | Ingram | 137/253 X |
| 3,110,173 | 11/1963 | Bishop | 73/77 |
| 3,532,270 | 10/1970 | Schoen, Jr. | 236/44 R |
| 3,712,140 | 1/1973 | Grasso et al. | 73/338 |
| 3,890,828 | 6/1975 | Pleva | 73/29 |
| 4,129,250 | 12/1978 | Chaikin | 236/44 A |
| 4,461,167 | 7/1984 | Kent et al. | 73/29 |
| 4,502,288 | 3/1985 | Lynch | 62/171 |

*Primary Examiner*—William E. Wayner
*Attorney, Agent, or Firm*—Flehr, Hohbach, Test, Albritton & Herbert

[57] ABSTRACT

System and method for continuously monitoring the wet bulb temperature in a flue gas stream, for example, at the inlet of a spray dryer. A sample of the flue gas is filtered and reheated to substantially the same temperature as the gas in the flue. The temperature of the reheated sample is measured with a sensor surrounded by a liquid absorbant wick, immersed in liquid maintained at a substantially constant level in a reservoir.

15 Claims, 1 Drawing Sheet

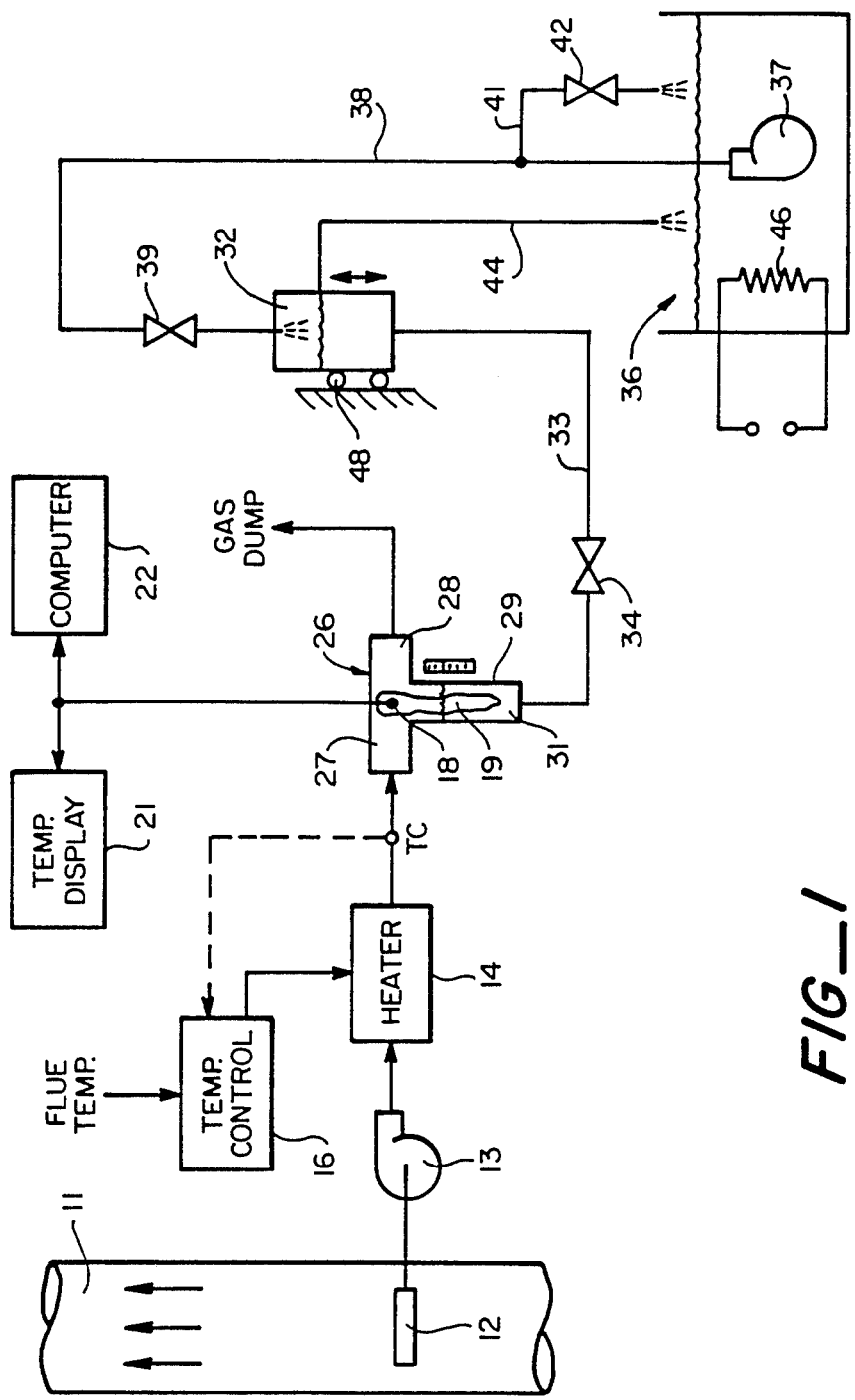
FIG_1

SYSTEM AND METHOD FOR MONITORING WET BULB TEMPERATURE IN A FLUE GAS STREAM

This invention pertains generally to temperature measurement, and more particularly to a system and method for monitoring the wet bulb temperature in a flue gas stream as found, for example, at the inlet to a spray dryer.

Spray dryers are employed in electric power generating plants to remove $SO_2$ and other contaminants from the exhaust gases of coal burning turbine-generators. In order to operate the spray dryers in their most efficient range, the wet bulb temperature of the incoming gas must be monitored closely.

In the past, the wet bulb temperature at the inlet to spray dryers has been monitored manually. This technique is costly from a labor standpoint, and it has the further disadvantage of not permitting the gas stream temperature to be monitored on a continuous basis. Continuous monitoring is desirable because it permits better control over the spray dryer approach to saturation (outlet temperature minus wet bulb temperature) and more efficient operation of the dryer.

U.S. Pat. No. 4,129,250 discloses a system which is intended for use in the continuous measurement and control of the relative humidity of exhaust gas from industrial dryers. This system employs both wet and dry bulb sensors, with means for periodically dipping the wet bulb sensor into a container of water. A voltage developed from the sensors provides a measure of the relative humidity and is utilized to control the amount of air discharged from the dryer to the atmosphere. After each dipping of the sensor, the application of the control voltage must be delayed until the wet bulb sensor reaches equilibrium with the exhaust gas. Variations in the wetness of the sensor can also affect the temperature and humidity readings. While this system may provide some measure of automated control over the relative humidity of the exhaust gas, it does have certain limitations and disadvantages, and it does not provide a continuous readout of the wet bulb temperature which is needed to efficiently control the spray dryer operation.

It is in general an object of the invention to provide a new and improved system and method for monitoring the wet bulb temperature in a flue gas stream.

Another object of the invention is to provide a system and method of the above character which overcome the limitations and disadvantages of systems and methods heretofore provided for measuring wet bulb temperature.

These and other objects are achieved in accordance with the invention by extracting a sample of the flue gas, filtering the sample, heating the filtered sample to maintain it at substantially the same temperature as the gas in the flue, measuring the temperature of the heated sample with a sensor surrounded by a liquid absorbant wick, applying liquid to the wick from a reservoir, and maintaining the liquid in the reservoir at a substantially constant level. Liquid is supplied to the reservoir from a second reservoir, with the level of the liquid in the first reservoir being dependent upon the level of the liquid in the second reservoir. Liquid is supplied continuously to the second reservoir to maintain it in an overflow condition, and this maintains the liquid at substantially constant levels in both the first reservoir and the second reservoir.

The single FIGURE of drawing is a schematic diagram of one embodiment of a system for monitoring the wet bulb temperature of a flue gas stream in accordance with the invention.

In the drawing, the invention is illustrated in connection with a flue 11 at the inlet to a spray dryer (not shown) for cleaning the exhaust gas of a coal burning turbine-generator at an electric power generating station.

Means is provided for continuously extracting a sample from the gas stream in the flue. This means includes a filter 12 mounted within the flue and a pump 13 which draws the sample through the filter. In one presently preferred embodiment, the filter comprises a sintered, stainless steel filter, and the pump comprises an insulated diaphragm pump. The filter serves to remove solid contaminants such as fly ash from the gas sample.

The filtered gas sample is pumped to a heater 14 where it is reheated to substantially the same temperature as the gas in the flue. In a preferred embodiment, the heater comprises a low voltage nichrome heater. A temperature control 16 monitors the temperature of the gas in the flue and at the output of the heater and controls the operation of the heater to make the output temperature equal to the flue temperature.

The wet bulb temperature of the reheated gas sample is measured by a thermocouple sensor 18 surrounded by a liquid absorbant wick 19. The temperature measured by the sensor is displayed by a thermocouple signal processing the sensor is also supplied to a computer 22 in a data acquisition system.

Sensor 18 and wick 19 are mounted in a T-shaped vessel 26 having a pair of horizontally extending arms 27, 28 and a depending arm or reservoir 29. The gas sample is introduced into the T-shaped vessel through arm 27 and exhausted through arm 28, and wick 19 extends into reservoir 29 where it is immersed in a suitable liquid 31 such as water. Liquid absorbed by the wick wets the thermocouple sensor to provide the desired wet bulb reading.

Means is provided for maintaining the liquid in reservoir 29 at a substantially constant level. This is important from the standpoint of accurate temperature readings. If the level is too high or too low, insufficient liquid will be supplied to the sensor, and the temperature readings will vary.

The means for maintaining the substantially constant liquid level includes a second reservoir 32 which is connected in fluid communication with reservoir 29 by a line 33 which extends between the lower portions of the two reservoirs. A flow control valve 34 is provided in line 33. Water is supplied to reservoir 32 from a tank 36 by a pump 37 and a line 38. A flow control valve 39 in line 38 controls the rate at which the water is delivered to reservoir 32. A by-pass line 41 having a flow control valve 42 is connected to line 38 for returning excess water from pump 37 to tank 36. An overflow line 44 is connected to reservoir 32 for returning water above a predetermined level in this reservoir to tank 36. By maintaining reservoir 32 continuously in an overflow condition, the water in this reservoir is maintained at a substantially constant level, the overflow level.

A heater 46 is provided for heating the water in tank 36 and, hence, the water applied to sensor 18.

The level of the water in reservoir 29 is dependent upon the level of the water in reservoir 32 and the relative pressures above the water in reservoirs 32 and 29. The level in reservoir 29 can be changed by raising or lowering reservoir 32 and by adjusting the rate at which water is delivered to this reservoir. Reservoir 32 is mounted on an adjustable mount 48, and coarse adjustments of the water level are made by means of this mount. Finer adjustments are made by means of inlet valve 39, and small changes in the rate of water flow into reservoir 32 will result in small changes in static head at the overflow point. These water level adjustments are made on a periodic basis to compensate for static pressure differences in the flue, and hence in the gas sample, due to boiler load variations.

Operation and use of the monitoring system, and therein the method of the invention, are as follows. A gas sample is extracted from the flue through filter 12 and reheated by heater 14 to substantially the same temperature as the gas in the flue. The wet bulb temperature of the reheated gas sample is monitored by sensor 18 and displayed.

As the water in reservoir in 29 is consumed by the wicking action and by evaporation at the wet bulb sensor, it is replenished from reservoir 32. Water is supplied to reservoir 32 from tank 36 at a rate which is sufficient to maintain reservoir 32 in an overflow condition. As long as reservoir 32 is in an overflow condition, the water level in this reservoir is substantially constant, and this keeps the water level in reservoir 29 substantially constant. The water level in reservoir 29 can be adjusted by raising or lowering reservoir 32 or by increasing or decreasing the rate of flow into reservoir 32.

It is apparent from the foregoing that a new and improved system and method for monitoring the wet bulb temperature in a flue gas stream have been provided. While only certain presently preferred embodiments have been described in detail, as will be apparent to those familiar with the art, certain changes and modifications can be made without departing from the scope of the invention as defined by the following claims.

We claim:

1. In a system for monitoring the wet bulb temperature in a flue gas stream: means for extracting a sample of the gas from the flue, means for heating the sample to maintain the sample at substantially the same temperature as the gas in the flue, a sensor for measuring the wet bulb temperature of the sample, a reservoir of liquid, a liquid absorbant wick surrounding the sensor and extending into the liquid in the reservoir, and means for maintaining the liquid in the reservoir at a substantially constant level, said means for maintaining the liquid at a substantially constant level comprising a second reservoir in fluid communication with the first named reservoir and adapted to overflow when filled to a predetermined level, and means for supplying liquid to the second reservoir so that it overflows continuously and the liquid remains at the predetermined level in the second reservoir.

2. The system of claim 1 wherein the means for extracting a sample of the gas includes a filter and a pump.

3. The system of claim 1 wherein the sensor comprises a thermocouple.

4. The system of claim 1 wherein the means for maintaining the liquid in the reservoir at a substantially constant level comprises a second reservoir in fluid communication with the first named reservoir and adapted to overflow when filled to a predetermined level, and means for supplying liquid to the second reservoir so that it overflows continuously and the liquid remains at the predetermined level in the second reservoir.

5. The system of claim 1 including means for adjusting the level of the liquid in the first named reservoir.

6. The system of claim 5 wherein the means for adjusting the level of the liquid includes means for changing the vertical position of the second reservoir.

7. The system of claim 5 wherein the means for adjusting the level of the liquid includes means for varying the rate at which the liquid is supplied to the second reservoir.

8. In a system for monitoring the wet bulb temperature of gas in a flue: means for extracting a sample of the gas from the flue, means for heating the sample to maintain the sample at substantially the same temperature as the gas in the flue, a sensor for measuring the wet bulb temperature of the sample, a liquid absorbant wick surrounding the sensor, a first liquid reservoir into which the wick extends, a second liquid reservoir which overflows when filled to a predetermined level, means connecting the first and second reservoirs in fluid communication with each other so that the level of liquid in the first reservoir is dependent upon the level of liquid in the second reservoir, and means for supplying liquid to the second reservoir so that it overflows and the liquid in the first reservoir remains at a substantially constant level.

9. The system of claim 8 including means for changing the overflow level for the liquid in the second reservoir to adjust the level of the liquid in the first reservoir.

10. The system of claim 9 wherein the means for changing the overflow level includes means for raising or lowering the second reservoir.

11. The system of claim 8 including means for adjusting the level of the liquid in the first reservoir by controlling the rate at which liquid is supplied to the second reservoir.

12. In a method of monitoring the wet bulb temperature of a flue gas stream, the steps of: extracting a sample of the gas from the flue, heating the sample to maintain the sample at substantially the same temperature as the gas in the flue, measuring the wet bulb temperature of the sample with a sensor surrounded by a liquid absorbant wick, applying liquid to the wick from a reservoir, and maintaining the liquid in the reservoir at a substantially constant level by supplying liquid to the reservoir from a second reservoir in such manner that the level of liquid in the first named reservoir is dependent upon the level of liquid in the second reservoir, and continuously supplying liquid to the second reservoir to maintain the second reservoir in an overflow condition with the liquid at a substantially constant level in each of the two reservoirs.

13. The method of claim 12 including the step of changing the vertical position of the second reservoir to adjust the level of the liquid in the first named reservoir.

14. The method of claim 12 including the step of varying the rate at which the liquid is supplied to the second reservoir to control the level of the liquid in the first named reservoir.

15. In a method of monitoring the wet bulb temperature of a flue gas stream, the steps of: extracting a sample of the gas from the flue, heating the sample to maintain the sample at substantially the same temperature as the gas in the flue, measuring the wet bulb temperature of the sample with a sensor surrounded by a liquid absorbant wick, applying liquid to the wick from a reservoir, maintaining the liquid in the reservoir at a substantially constant level, and filtering the sample extracted from the flue to remove impurities from the sample.

* * * * *